United States Patent
Waiche et al.

(10) Patent No.: US 9,315,850 B2
(45) Date of Patent: Apr. 19, 2016

(54) MEMBRANE TRANSFER METHOD AND TOOL

(75) Inventors: Gael Waiche, Molsheim (FR); Monika Kukuczka, Andlau (FR)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/521,066

(22) PCT Filed: Jan. 12, 2011

(86) PCT No.: PCT/IB2011/050134
§ 371 (c)(1),
(2), (4) Date: Jul. 9, 2012

(87) PCT Pub. No.: WO2011/086508
PCT Pub. Date: Jul. 21, 2011

(65) Prior Publication Data
US 2013/0059326 A1    Mar. 7, 2013

(30) Foreign Application Priority Data

Jan. 14, 2010 (FR) ..................................... 10 50233

(51) Int. Cl.
*C12Q 1/24* (2006.01)
*C12M 1/26* (2006.01)
*C12M 1/30* (2006.01)

(52) U.S. Cl.
CPC ............... *C12Q 1/24* (2013.01); *C12M 33/02* (2013.01); *C12M 33/14* (2013.01)

(58) Field of Classification Search
CPC .......... C12Q 1/24; C12M 33/14; C12M 33/02
USPC ............................................. 435/30; 436/174
See application file for complete search history.

(56) References Cited

U.S. PATENT DOCUMENTS 3,929,583 A * 12/1975 Sharpe et al. ............... 435/288.5
4,777,137 A * 10/1988 Lemonnier ................. 435/288.1

(Continued)

FOREIGN PATENT DOCUMENTS

CN    2923714 Y    7/2007
FR    2558847 A1   8/1985

OTHER PUBLICATIONS

Oxford University Press Dictionary, http://www.oxforddictionaries.com/us/definition/learner/pad.*
International Search Report/Written Opinion mailed Mar. 28, 2011 in corresponding PCT application No. PCT/IB2011/050134.
International Preliminary Report on Patentability mailed Jul. 26, 2012 in corresponding PCT application No. PCT/IB2011/050134.

(Continued)

*Primary Examiner* — Jill Warden
*Assistant Examiner* — Julie Tavares
(74) *Attorney, Agent, or Firm* — Nields, Lemack & Frame, LLC (57) ABSTRACT

A method for transferring a filter membrane (130) bearing a retentate to a reagent pad (310), in which the membrane is mounted in a support frame (120) having a shoulder (121) and a skirt (122) projecting from the shoulder, the pad being mounted on a cassette (300) of complementary form to said skirt, the skirt being adapted to slide sealingly on the cassette until it comes into abutment formed by the shoulder, the method comprising the steps of sealingly engaging the skirt of the membrane support frame on the cassette, establishing a pressure difference between the cassette and the membrane support frame such that the membrane adopts the shape of a dome pointing towards the pad, while maintaining the pressure difference, applying a force on the frame so as to make the skirt slide on the cassette until contact is established between the end of the dome and the pad, maintaining a force on the frame so as to move it downward until it comes into abutment formed by the shoulder while maintaining the pressure difference.

7 Claims, 5 Drawing Sheets

(56) References Cited

U.S. PATENT DOCUMENTS

| | | | |
|---|---|---|---|
| 6,287,849 B1 | 9/2001 | McNerney et al. | |
| 2002/0192739 A1* | 12/2002 | Lemonnier | 435/30 |
| 2008/0268422 A1* | 10/2008 | Olivier et al. | 435/4 |
| 2014/0017779 A1 | 1/2014 | Waiche et al. | |

OTHER PUBLICATIONS

Office Action mailed Aug. 4, 2015 in corresponding U.S. Appl. No. 14/036,339.

Final rejection mailed Feb. 1, 2016 in co-pending U.S. Appl. No. 14/036,339.

* cited by examiner

MEMBRANE TRANSFER METHOD AND TOOL

The present invention generally relates to the field of the microbiological testing of liquids.

More particularly, the present invention concerns a method referred to as membrane filtration. This method consists of filtering a liquid sample on a porous membrane and then of depositing the membrane on gel growth media. The assembly is next incubated in order for the microorganisms of the sample retained on the membrane during filtration to be able to develop sufficiently to be visible to the naked eye. This simple method enables the microorganisms present in the sample to be counted and so to determine the degree of contamination thereof.

Filter membrane devices are known which enable this method to be implemented.

Document FR 2558847 describes a filter device having a tubular sleeve for containing a sample, and of which the base is constituted by a filter membrane, fixed to the end of the sleeve in a female end fitting forming a holding frame for the membrane and adapted to cooperate with a receptacle containing a growth medium. Once the filtration has been carried out, a fluid-tight cover is placed on the opposite end of the sleeve, the effect of which is to compress a small amount of air in the sleeve and push on the membrane which then adopts the shape of a dome pointing outwardly of the sleeve. The sleeve is then placed on the growth medium, and the membrane enters into contact with the growth medium from its center towards the outside, so minimizing the risk of bubble formation.

Once the membrane is in contact with the growth medium, the sleeve may be separated from the end fitting bearing the membrane. The end fitting is next provided with a protective cover and then the assembly is incubated.

In practice, the surface area of a membrane increases when it passes from a dry state to a wet state. This is what occurs further to the filtering step. Furthermore, the growth medium on which the membrane is then deposited has the shape of a dome pointing towards the membrane. Thus, on incubation, the membrane deforms by creep in contact with the growth medium: its surface area further increases relative to that obtained on finishing the filtering step.

In certain microbiological analyses, it is necessary to apply a reagent to the membrane after having incubated it. This may, for example, be a revealing reagent. For this, a substantially flat pad is used, which is impregnated with the chosen reagent before depositing the membrane thereon, which has been separated from the growth medium beforehand.

In practice, this poses several problems:
  further to the filtration and the incubation, the surface area of the membrane is greater than that of the reagent pad,
  the radius of curvature of the membrane and that of the pad do not match,
  the sleeve is no longer in place and it is therefore no longer possible to apply additional pressure to give the membrane the shape of a dome pointing outwardly,
  the cover that is applied before incubation cannot be removed to avoid possible contamination by the external air.

The present invention aims to overcome these problems to enable a reagent to be applied, via a substantially flat pad, to the membrane deformed after filtration and incubation. To that end it provides a method for transferring a filter membrane bearing a retentate to a reagent pad, in which the membrane is mounted in a support frame having a shoulder and a skirt projecting from the shoulder; the pad being mounted on a cassette of complementary form to said skirt; the skirt being adapted to slide sealingly on the cassette until it comes into abutment formed by the shoulder; the method comprising the steps of sealingly engaging the skirt of the membrane support frame on the cassette, establishing a pressure difference between the cassette and the membrane support frame such that the membrane adopts the shape of a dome pointing towards the pad; while maintaining the pressure difference, applying a force on the frame so as to make the skirt slide on the cassette until contact is established between the end of the dome and the pad; and maintaining a force on the frame so as to move it downward until it comes into abutment formed by the shoulder while maintaining the pressure difference.

Thus, according to an advantageous result of the invention, further to this method, the membrane has returned to its original dimensions, substantially identical to those of its support frame while having been applied from a substantially central point outwardly of the pad, thereby avoiding the formation of bubbles.

As a matter of fact, even when humid and bearing a retentate, the membrane has a certain degree of stiffness. The fact of applying a pressure difference between the opposite sides of the membrane enables it to be given the shape of a dome pointing towards the pad. This enables the pad to be contacted at a substantially central point when the downward movement occurs. Once this first contact zone has been established, contact friction is created between the membrane and the impregnated pad on that contact area. As the membrane has a certain stiffness of its own, the fact of applying a force on the frame to move the membrane downward against the pad results in a radial centripetal compression force of the membrane along the line delimiting the area of contact of the membrane with the pad.

In other words, once the contact area has been established, the friction existing between the membrane and the pad over that area is taken advantage of to supply, on the line delimiting that surface, a centripetal force compressing the membrane towards the center while the membrane is in course of being applied to the pad. This force results from the force applied to the frame. This force is transmitted towards the contact area by virtue of the membrane's own stiffness. The pressure difference contributes to keeping the membrane domed and stiffened to avoid it collapsing on itself even when that force is applied.

Thus, the method according to the invention enables the problems set out above to be solved: the membrane is uniformly applied onto the pad, while limiting the risk of forming bubbles, and, further to the operation, the surface area of the membrane substantially returns to its original surface area, itself substantially identical to the surface area of the pad.

According to other features, which may be combined:
  the pressure difference is a pressure reduction applied in a space between the membrane and the cassette.
  the method is preceded by a step of saturating the pad with a reagent.
  the reagent is a solution adapted to reveal the microorganisms contained in the retentate of the membrane.

According to another aspect, the present invention concerns a tool for transferring a filter membrane bearing a retentate to a reagent pad, in which the membrane is mounted in a support frame having a shoulder and a skirt projecting from the shoulder, the pad is mounted on a cassette of complementary form to said skirt, the skirt being adapted to slide sealingly on the cassette until it comes into abutment formed by the shoulder, the membrane transfer tool comprising a tool body with a free end adapted to receive said reagent cassette, an ejection head mounted for translational movement relative to the body, adapted to bear on the cassette to eject the latter, a means for actuating the head in translational movement, means for sealing and retention disposed on the tool body so as to sealingly retain the cassette on the tool body, means for applying a pressure difference between the cassette and the body of the tool.

According to advantageous features, which may be combined:

the means for applying a pressure difference between the cassette and the body of the tool are an opening formed in the body of the tool, adapted to be connected to a vacuum pump that is external to the tool, and at its other end opening into a fluid-tight space between the cassette and the body of the tool.

the ejection head is annular and surrounds the body of the tool.

Thus, advantageously, the ejection force is produced uniformly distributed around the periphery and there is no deformation of the cassette or the frame so enabling good adhesion between the membrane and the pad, once the membrane is in contact therewith.

According to advantageous features, which may be combined:

the tool further comprises integrated means for pressure regulation.

the pressure regulation means are tared for a pressure between 40 and 70 millibars.

Thus, advantageously, these provisions make it possible to avoid applying too high a pressure so as not to deform the membrane, while maintaining an optimum pressure to achieve compression of the membrane when it is applied to the pad so that the membrane substantially returns to its original dimensions. Furthermore, this device enables the possible variations resulting from an irregular operation of the vacuum pump to be expunged.

According to an advantageous feature of the invention, means for sealing and retention disposed on the tool body so as to sealingly retain the cassette on the tool body are a seal inserted into a groove formed in the body for that purpose.

This construction is particularly simple and the function of sealing and mechanical retention of the cassette on the tool is provided by the same member.

According to an advantageous feature, the means for actuating the head in translational movement are an ejection lever. This enables the ejection force to be increased.

According to another aspect, the present invention concerns a method for implementing a tool as described above, which comprises the steps of:

placing the cassette on the tool so as to engage the means for sealing and retention that are provided for that purpose, impregnating the pad with reagent, starting the means for applying a pressure difference between the cassette and the body of the tool, sealingly engaging the skirt of the membrane support frame on the cassette;

establishing a pressure difference between the cassette and the membrane support frame such that the membrane takes the form of a dome pointing towards the pad;

while maintaining the pressure difference, applying a force on the frame so as to make the skirt slide on the cassette until contact is established between the end of the dome and the pad;

maintaining a force on the frame so as to make the frame move downward until it comes into abutment formed by the shoulder while maintaining the pressure difference.

According to an advantageous feature, the cassette has openings enabling air to pass through the cassette and the establishment of a pressure difference between the cassette and the membrane support frame such that the membrane takes the form of a dome pointing towards the pad is generated by the means for applying a pressure difference between the cassette and the body of the tool by passing air between the tool and the membrane via the cassette.

The invention will be better understood on reading the description of an embodiment of a tool and of the implementation of a method according to the invention, with reference to the accompanying drawings, given by way of non-limiting example, and in which.

Figure 1:
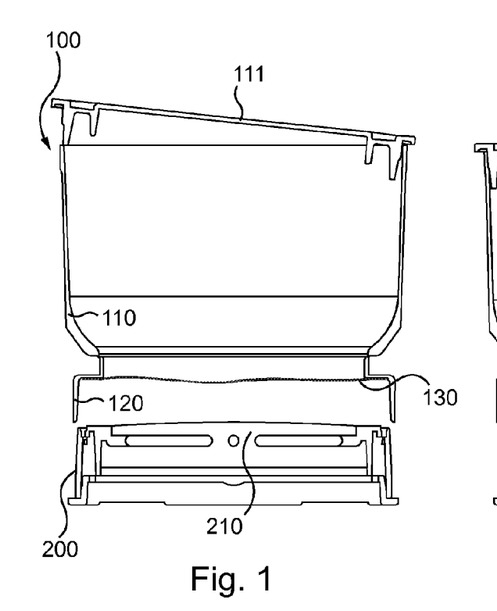
FIGS. 1 to 3 are diagrammatic views in cross-section of a known microbiological analysis device.
Figure 2:
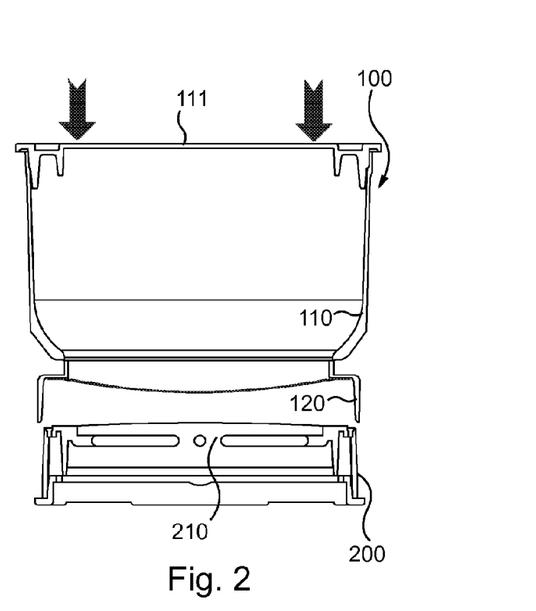

As can be seen more particularly in FIGS. 1 and 2, a filtration device 100 has a tubular sleeve 110 joined to a holding frame 120 for a membrane 130 adapted to cooperate with a cassette 200 containing a growth medium 210. A sample of a liquid not shown is introduced into the sleeve 110 then filtered through the filter membrane 130. Once the filtration has been carried out, the membrane 130 bearing the retentate passes from a dry state to a humid state which slackens it so increasing its surface area relative to its initial surface area. This is more particularly visible in FIG. 1.

In order to deposit the membrane 130 on the growth medium 210, the sleeve is closed using a fluid-tight cover 111. The closing of this cover enables a small quantity of air to be compressed within the sleeve which then exerts a pressure on the membrane the effect of which is to push the membrane outwardly giving it the shape of a some pointing outwardly of the sleeve as can be seen in FIG. 2. The sleeve may then be placed on the growth medium 210 without risking the formation of bubbles. Indeed, as can be seen in FIGS. 1 and 2, the growth medium 210 has the form of a dome pointing towards the sleeve. The contact between the membrane 130 and the growth medium 210 will occur first of all by the center then will extend outwardly, so limiting the risk of bubble formation and ensuring optimal adhesion of the membrane bearing the retentate from the filtration with the growth medium.

Figure 3:
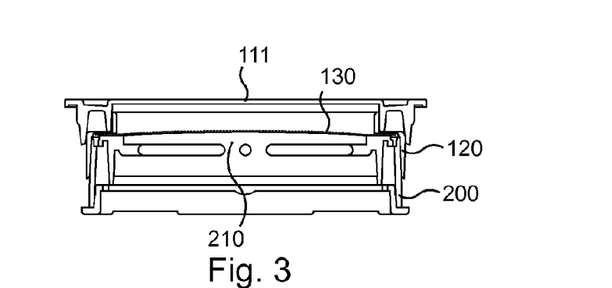

Once the contact has been established between the membrane 130 and the growth medium 210, the sleeve 110 is separated from the holding frame 120 for the membrane 130 and the cover 111 is disposed on the frame in order to protect the membrane 130 against possible contaminations. The assembly formed by the cassette 200 containing the growth medium 210, the frame 120 supporting the membrane 130 and the cover 111 as can be seen in FIG. 3 is then incubated for a period generally from 6 to 24 hours.

During this incubation, the microorganisms contained in the retentate develop until they are visible to the naked eye: they may thus be counted and the degree of contamination of the sample may thus be determined. However, during this period of incubation, as the growth medium is domed, the membrane 130 deforms by creep in contact therewith. Once the incubation has termination, the assembly formed by the frame 120 and the cover 111 is separated from the growth medium cassette 200 to be applied to a cassette 300 on which a pad 310 is mounted using a transfer method according to the invention.

As may be noted, further to the filtration and the creep, the membrane 130 is strongly distended and has a surface area very much greater than its original surface area.

Figure 4:
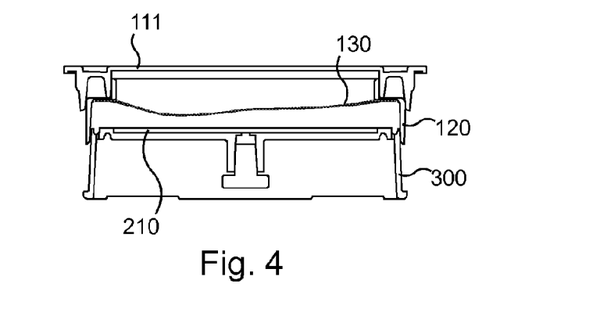
FIG. 4 is a view of a membrane support frame mounted on a complementary cassette.

As can be seen in FIG. 4, this poses a certain number of problems, preventing the membrane from being applied to the pad. To be precise, the geometry of the membrane 130 is very different from the geometry of the pad 310, the sleeve 110 is no longer available to give the membrane a dome shape and the cover 111 cannot be removed to avoid any contamination.

The transfer method according to the invention enables the membrane 130 to be transferred onto the pad 310 without forming bubbles in a simple, uniform and even manner.

Figure 5:
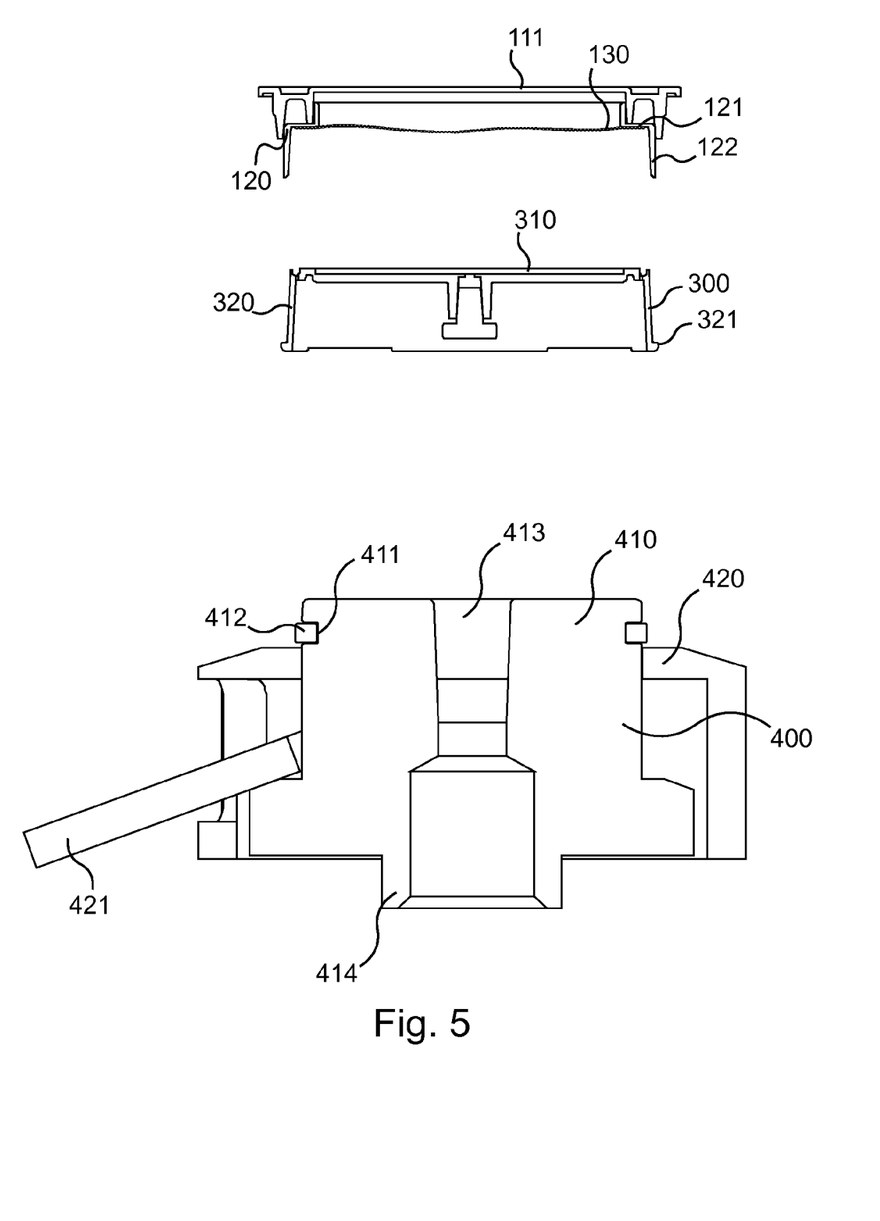
FIG. 5 is an exploded view of a tool according to the invention with a cassette and a membrane support.

This is made possible by the use of a stack of devices as can be seen in FIG. 5 et seq. A tool 400 for transferring a filter membrane bearing a retentate to a pad 310 according to the invention is adapted to receive a cassette 300 which is itself surmounted by an assembly formed by a membrane support frame 120 and a cover 111.

As can be seen more particularly in FIG. 5, the membrane 130 is mounted in a support frame 120 having a shoulder 121 and a skirt 122 projecting from the shoulder. The cassette 300 bearing the pad 310 has a conical outer shape 320 of complementary shape to the skirt 122 enabling the latter to slide sealingly on the cassette until it comes into abutment formed by the shoulder 121. This can be seen more particularly in FIGS. 9 to 12. The tool 400 for transfer of the membrane 130 to the pad 310 has a tool body 410 with a free end adapted to receive the cassette 300 and an annular ejection head 420 mounted for translational movement about the body 410. The ejection head is adapted to move relative to the tool body so as to bear on a lower rim 321 of the outer surface of the cassette to eject the latter. The translational movement of the ejection head relative to the body is actuated by means of an actuating lever 421 which enables the ejection force to be increased. The tool body 410 has a groove 411 at its free end which is dimensioned to receive a fluid-tight seal 412. The fluid-tight seal 412 and the groove 411 conjointly form means for sealing and retention of the cassette 300 once the latter has been introduced onto the tool. To be precise, the elasticity of the seal 412 contributes to mechanically holding the cassette 300 in place.

The body 410 of the tool 400 furthermore has a transverse opening 413 adapted to be connected by an end fitting 414 to an exterior pumping device not shown, enabling a reduction in pressure to be created in that opening which at its opposite end opens at the free end of the tool body adapted to receive the cassette 300. Thus, this opening enables a reduction in pressure to be applied between the cassette and the tool body.

Figure 6:
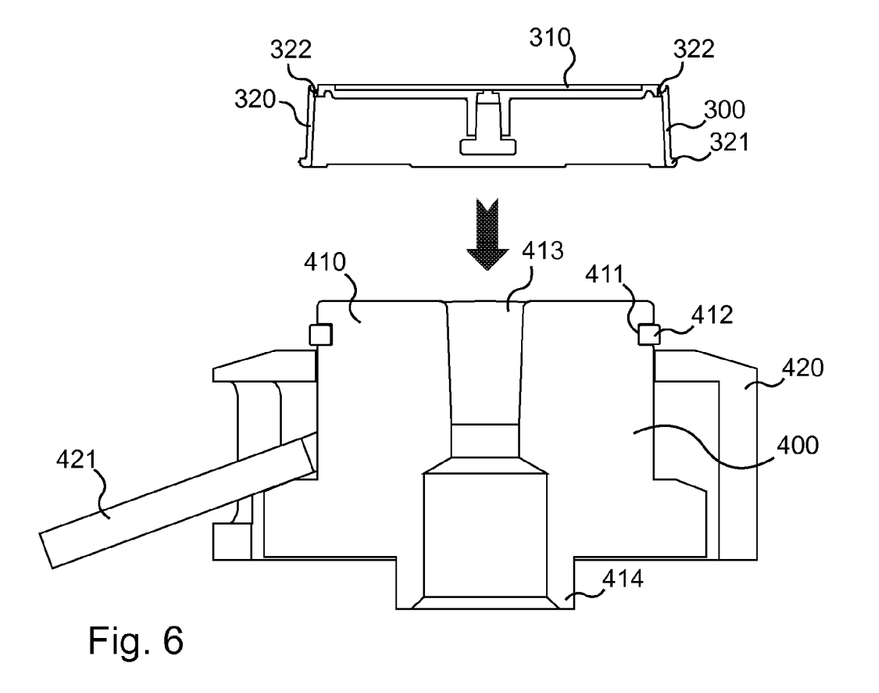
FIGS. 6 to 13 are the successive steps of use of the device represented in FIG. 5 in a method of microbiological analysis according to the invention.
Figure 7:
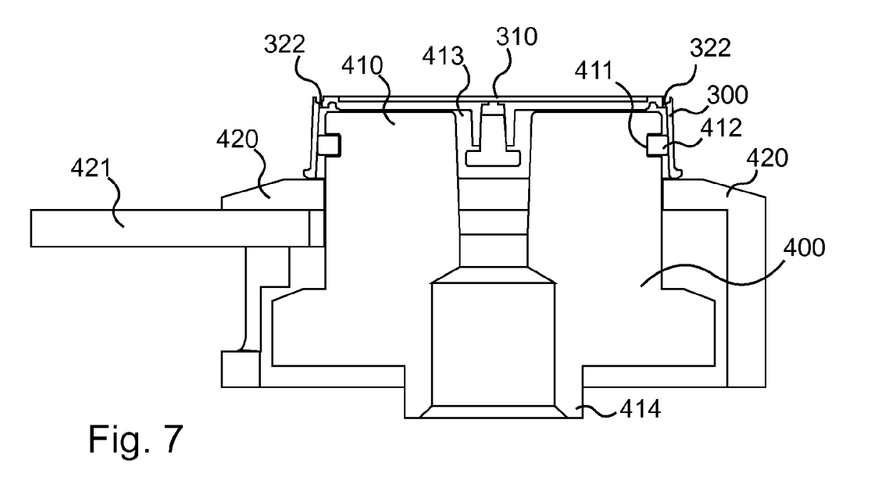

As can be seen in FIG. 6, the method of transferring a membrane according to the invention consists, in a first phase, of disposing the cassette 300 on the tool body 410. This introduction is carried out until abutment formed by the inner face of the cassette 300 and the free end of the body 410 of the tool 400 is attained. The effect of this insertion is to move the ejection head down relative to the body 410 as can be seen in FIG. 7. By this same movement, the actuating lever 421 rises to a substantially horizontal position.

A protective film, not shown, which is disposed on the pad 310 may then be removed and the buffer is saturated with a solution of reagents. In the present embodiment, this is a solution adapted to reveal the microorganisms contained in the retentate of the membrane.

Figure 8:
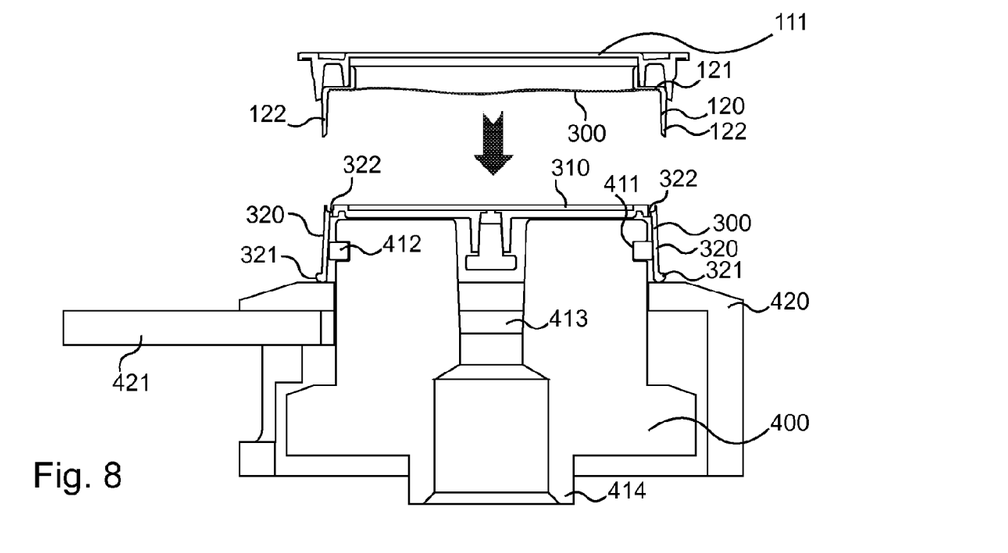

As can be seen more particularly in FIG. 8, the membrane support frame 120 is then disposed on the cassette 300. The vacuum pump connected to the opening 413 is then started, and generates suction between the cassette 300 and the seal 412. As can be seen in FIG. 8, the cassette has, on its upper part on the periphery of the pad 310, a plurality of openings 322 enabling air to communicate between the space defined by the seal 412, the lower face of the cassette 300 and the outside.

Figure 9:
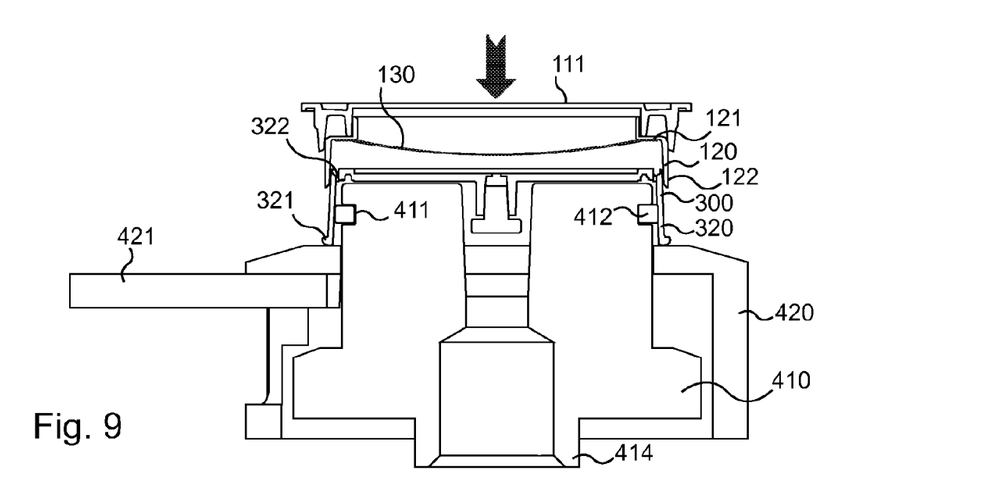
Figure 10:
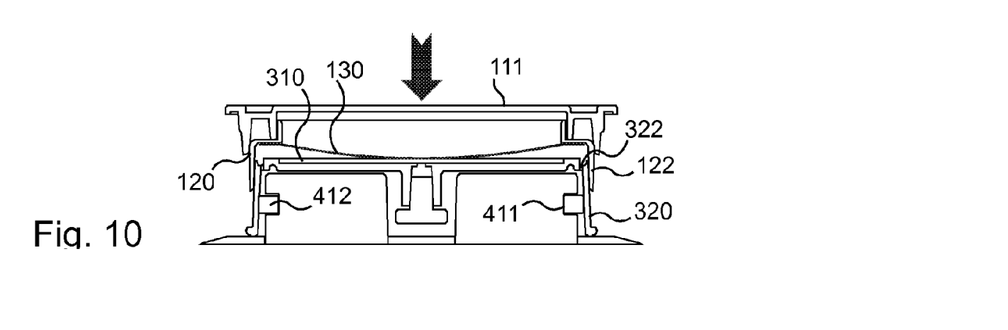

As can be seen in FIG. 9, the membrane support frame is then mounted on the cassette 300. As the skirt 122 then sealingly cooperates with the conical outer surface 320 of the cassette, a pressure difference between the two faces of the membrane arises via the openings 322. This then takes the form of a dome pointing towards the pad as may be seen in FIG. 9. As can be seen in FIG. 10, a force diagrammatically represented by an vertical arrow is applied to the membrane support frame 120 via the cover 111 the effect of which is to make the skirt 122 slide relative to the cassette. A substantially central contact area between the membrane and the pad is then established.

Figure 11:
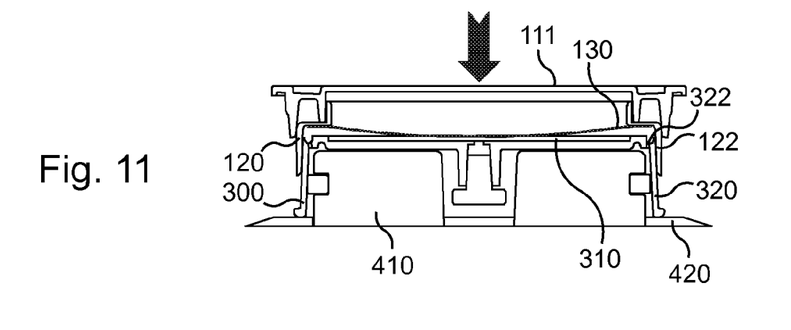
Figure 12:
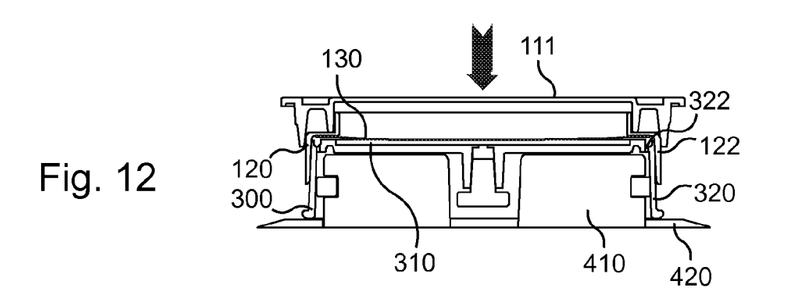

While maintaining the pressure difference between the opposite sides of the membrane, the compression force is continuously applied on the membrane support frame as visible in FIGS. 11 and 12, so as to transfer the membrane onto the pad progressively from the central contact area outwards.

During these steps represented in FIGS. 10 to 12, the membrane is progressively compressed towards its center and further to this operation it has returned to its original dimensions. Applying a pressure difference between the opposite sides of the membrane gives it the shape of a dome pointing towards the pad. The membrane moreover has a certain stiffness of its own. Once a first contact zone has been established between the membrane and the pad, the force applied to the frame 120 combined with a contact friction arising between the membrane and the pad on that first contact zone results in a radial centripetal compression force experienced by the membrane along the line delimiting the contact area between the membrane and the pad. The membrane's own stiffness combined with the pressure difference providing a membrane shape which is domed towards the pad enables a progressive compression effect of the membrane towards the center as its application to the pad advances, as can be seen in FIGS. 10 to 12.

To attain this result, it is necessary to apply a predetermined pressure difference preferably within a range from 40 to 70 millibars. Ideally, this pressure is 50 millibars. To keep this pressure at this value, the body of the tool 410 is provided with a pressure regulating device, not shown, which enables the pressure difference to be held constant between the opening 413 and the outer environment so as to expunge possible variations in pressure which could be generated by the vacuum pump connected to the end fitting 414. To be precise, too low a pressure would not enable the membrane to be sufficiently stiffened which would then collapse on itself under the application of the force, and too high a pressure would on the contrary have a tendency to deform the membrane to enlarge its surface area still further. The force applied on movement of the frame must be sufficient to complete the path from the engagement of the skirt 122 on the cassette 300 until the abutment constituted by the shoulder 121 and the upper part of the cassette 300 is attained, this distance in practice being of the order of 5 to 6 mm and having to be completed in a time greater than 0.6 seconds to attain that result.

Figure 13:
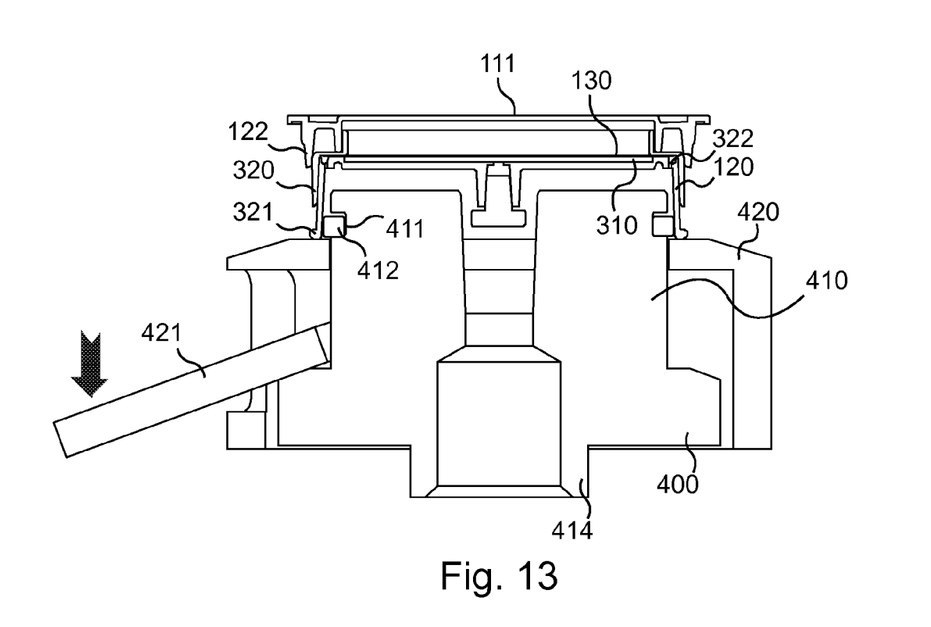

Once the membrane has been uniformly applied to the pad, it is necessary, for the subsequent operations of the microbiological analysis which will not be described in more detail here, to extract the assembly formed by the frame 120, by the cover 111 and by the cassette 300 of the tool 400. As can be seen in FIG. 13, the lever 421 is actuated for this purpose. The ejection head 420 then moves relative to the body of the tool 410 and comes to press uniformly on the lower edge 321 of the cassette 300. In this way, the extraction is achieved via a force having an even annular distribution around the periphery of the cassette which advantageously avoids applying torsional forces to it the effect of which could be to separate the membrane from the pad. Once extracted in this way, the assembly formed by the cassette, the cover and the frame is ready to be used in the subsequent part of the microbiological analyses.

Generally, it will be noted that in the example described above, all the components have a substantially circular cross-section. However, the formation of an assembly according to the invention having an oval or polygonal closed section is within the capability of the person skilled in the art without departing from the scope of the invention.

It should be observed that the tool 400 disclosed above is designed for transferring a filter membrane such as membrane 130 bearing a retentate to a reagent pad such as the pad 310 but that the tool 400, and more generally the tool according to the present invention, can be used for transferring a filter membrane to members different from a reagent pad, for instance:

a pad impregnated with a liquid substance different from a reagent, for instance a nutritive liquid medium; or a gel growth medium, such as a gel growth medium in a petri dish.

It should be also observed that the tool according to the invention can be used for transferring the membrane to a member which is not flat but with a curvature different from the curvature of the membrane, so as to assure a good contact between the membrane and the member.

Naturally, many modifications can be made to the embodiment described above without departing from the scope of the invention.

The invention claimed is:

1. A method of transferring a filter membrane bearing a retentate to a reagent pad, wherein:
   the membrane is mounted in a support frame having a shoulder and a skirt projecting from the shoulder;
   the pad having a membrane contact surface that is substantially flat, the pad being mounted on a cassette of complementary form to said skirt, the pad not being a gel growth medium;
   the skirt being adapted to slide sealingly on the cassette until it comes into abutment formed by the shoulder;
   the method comprising:
   sealingly engaging the skirt of the membrane support frame on the cassette;
   establishing a predetermined pressure difference between the cassette and the membrane support frame such that the membrane takes the form of a dome pointing towards the pad, said pressure difference being a pressure reduction applied in a space between the membrane and the cassette;
   while maintaining the pressure difference, applying a force on the frame so as to make the skirt slide on the cassette until contact is established between the end of the dome and the membrane contact surface of the pad;
   maintaining a force on the frame so as to make the frame move downward until it comes into abutment formed by the shoulder while maintaining the pressure difference, thereby uniformly transferring said filter membrane to said membrane contact surface of the pad.

2. A method according to claim 1, wherein it is preceded by saturating the pad with a reagent.

3. A method according to claim 2, wherein the reagent is a solution adapted to reveal the microorganisms contained in the retentate of the membrane.

4. A method according to claim 1, wherein said dome has a region comprising a central contact area, and wherein said maintenance of force on said frame transfers said membrane filter progressively from said central contact area radially outwards.

5. A method according to claim 1, wherein said predetermined pressure ranges from 40 to 70 millibars.

6. A method according to claim 1, wherein said pad is impregnated with a liquid.

7. A method according to claim 6, wherein said liquid is a reagent adapted to reveal the presence of microorganisms in said retentate.

* * * * *